US006497650B1

(12) United States Patent
Nicolo

(10) Patent No.: US 6,497,650 B1
(45) Date of Patent: Dec. 24, 2002

(54) HERNIA PROSTHESIS

(75) Inventor: Enrico Nicolo, Clairton, PA (US)

(73) Assignee: C. R. Bard, Inc., Murray Hill, NJ (US)

( * ) Notice: Subject to any disclaimer, the term of this patent is extended or adjusted under 35 U.S.C. 154(b) by 25 days.

(21) Appl. No.: 09/627,855

(22) Filed: Jul. 28, 2000

Related U.S. Application Data

(60) Provisional application No. 60/146,061, filed on Jul. 28, 1999.

(51) Int. Cl.[7] .............................. A61F 2/00; A61F 13/00

(52) U.S. Cl. ......................................................... 600/37

(58) Field of Search ...................... 600/37; 623/14.13, 623/11.11, 1.21, 13.11; 606/151, 108, 193, 215, 216; 424/426, 424; 602/46, 904, 44, 58

(56) References Cited

U.S. PATENT DOCUMENTS

| | | |
|---|---|---|
| 2,621,145 A | 12/1952 | Sano |
| 2,671,444 A | 3/1954 | Pease, Jr. |
| 3,054,406 A | 8/1962 | Usher |
| 3,272,204 A | 9/1966 | Artandi et al. |
| 3,625,209 A | 12/1971 | Clark |
| 4,051,848 A | 10/1977 | Levine |
| 4,400,833 A | 8/1983 | Kurland |
| 4,576,608 A | 3/1986 | Homsy |
| 4,585,458 A | 4/1986 | Kurland |
| 4,633,873 A | 1/1987 | Dumican et al. |
| 4,655,221 A | 4/1987 | Devereux |
| 4,693,720 A | 9/1987 | Scharnberg et al. |
| 4,725,279 A | 2/1988 | Woodroof |

(List continued on next page.)

FOREIGN PATENT DOCUMENTS

| | | |
|---|---|---|
| CA | 2114282 | 7/1994 |
| DE | 298 17 682 U1 | 4/1999 |

(List continued on next page.)

OTHER PUBLICATIONS

Goldstein, Harold, M.D., F.A.C.S.; atrium Polypropylene Mesh, "An Atlas of Hernia Repair Using an Inguinal Hernia Repair Preshape with Keyhole Slit", Atrium Medical Corporation, Jun. 1995, 5 pp.

(List continued on next page.)

*Primary Examiner*—Kevin Shaver
*Assistant Examiner*—Brian Szmal
(74) *Attorney, Agent, or Firm*—Wolf, Greenfield & Sacks, P.C.

(57) ABSTRACT

A prosthesis and a method for repairing a tissue or muscle wall defect, such as an inguinal hernia, near a cord-like structure, such as the spermatic cord. The prosthesis comprises a layer of repair fabric having a cord opening therethrough that is adapted to receive the cord-like structure when the prosthesis is implanted at the repair site. The prosthesis also includes a cord protector that is attachable to the repair fabric at the opening to isolate the cord-like structure from the fabric in proximity to the opening. The repair fabric may be formed from a material which is susceptible to the formation of adhesions with sensitive tissue and organs. The cord protector may be formed from material which inhibits the formation of adhesions with sensitive tissue and organs. The cord protector may overlie a portion of at least one of the first and second surfaces of the repair fabric. The cord protector may extend substantially farther away from the opening edge on one of the first and second surfaces than on the other of the first and second surfaces. The cord protector may be configured as an insert that is separate from and attachable to the repair fabric. Alternatively, the cord protector may be integral with the repair fabric to form a composite prosthesis.

43 Claims, 3 Drawing Sheets

U.S. PATENT DOCUMENTS

| | | | |
|---|---|---|---|
| 4,769,038 | A | 9/1988 | Bendavid et al. |
| 4,854,316 | A | 8/1989 | Davis |
| 4,882,162 | A | 11/1989 | Ikada et al. |
| 4,942,875 | A | 7/1990 | Hlavacek et al. |
| 4,997,440 | A | 3/1991 | Dumican |
| 5,002,551 | A | 3/1991 | Linsky et al. |
| 5,007,916 | A | 4/1991 | Linsky et al. |
| 5,092,884 | A | 3/1992 | Devereux et al. |
| 5,100,422 | A | 3/1992 | Berguer et al. |
| 5,104,400 | A | 4/1992 | Berguer et al. |
| 5,116,357 | A | 5/1992 | Eberbach |
| 5,116,360 | A | 5/1992 | Pinchuk et al. |
| 5,122,155 | A | 6/1992 | Eberbach |
| 5,141,515 | A | 8/1992 | Eberbach |
| 5,141,522 | A | 8/1992 | Landi |
| 5,147,374 | A | 9/1992 | Fernandez ................ 606/151 |
| 5,147,401 | A | 9/1992 | Bakker et al. |
| 5,222,987 | A | 6/1993 | Jones |
| 5,254,133 | A | 10/1993 | Seid |
| 5,258,000 | A | 11/1993 | Gianturco |
| 5,290,217 | A | 3/1994 | Campos |
| 5,292,328 | A | 3/1994 | Hain et al. ................ 606/151 |
| 5,326,355 | A | 7/1994 | Landi |
| 5,334,217 | A | 8/1994 | Das |
| 5,350,388 | A | 9/1994 | Epstein ................ 606/154 |
| 5,356,432 | A | 10/1994 | Rutkow et al. |
| 5,366,460 | A | 11/1994 | Eberbach |
| 5,368,602 | A | 11/1994 | de la Torre |
| 5,370,650 | A | 12/1994 | Tovey et al. |
| 5,379,754 | A | 1/1995 | Tovey et al. ................ 128/4 |
| 5,425,740 | A | 6/1995 | Hutchinson, Jr. |
| 5,433,996 | A | 7/1995 | Kranzler et al. |
| 5,456,720 | A | 10/1995 | Schultz et al. |
| 5,461,885 | A | 10/1995 | Yokoyama et al. |
| 5,480,436 | A | 1/1996 | Bakker et al. |
| 5,508,036 | A | 4/1996 | Bakker et al. |
| 5,519,004 | A | 5/1996 | Urry |
| 5,524,633 | A | 6/1996 | Heaven et al. ............ 128/749 |
| 5,569,273 | A | 10/1996 | Titone |
| 5,593,441 | A | 1/1997 | Lichtenstein et al. |
| 5,601,579 | A | 2/1997 | Semertzides |
| 5,614,284 | A | 3/1997 | Kranzler et al. |
| 5,634,931 | A | 6/1997 | Kugel |
| 5,695,525 | A | 12/1997 | Mulhauser et al. |
| 5,697,978 | A | 12/1997 | Sgro |
| 5,716,408 | A | 2/1998 | Eldridge et al. |
| 5,716,409 | A | 2/1998 | Debbas |
| 5,722,992 | A | 3/1998 | Goldman |
| 5,725,577 | A | 3/1998 | Saxon |
| 5,733,337 | A | 3/1998 | Carr, Jr. et al. |
| 5,743,917 | A | 4/1998 | Saxon |
| 5,766,246 | A | 6/1998 | Mulhauser et al. |
| 5,769,864 | A | 6/1998 | Kugel |
| 5,813,975 | A | 9/1998 | Valenti |
| 5,916,225 | A | 6/1999 | Kugel |
| 6,066,777 | A * | 5/2000 | Benchetrit ................ 623/11 |
| 6,258,124 | B1 * | 7/2001 | Darois et al. ............ 623/14.13 |
| 6,267,772 | B1 * | 7/2001 | Mulhauser et al. ......... 606/151 |

FOREIGN PATENT DOCUMENTS

| | | | |
|---|---|---|---|
| EP | 0 194 192 A1 | 9/1986 | |
| EP | 0 334 046 A2 | 2/1989 | |
| EP | 0 358 819 A1 | 3/1990 | |
| EP | 0 179 527 A1 | 7/1996 | |
| EP | 0 560 934 | 8/1996 | |
| EP | 0 827 724 A2 | 3/1998 | |
| EP | 0 537 769 | 4/1998 | ........... A61L/31/00 |
| EP | 0 362 113 | 4/1999 | |
| FR | 2 744 906 A1 | 8/1997 | |
| GB | 1 352 282 | 6/1972 | |
| GB | 1 406 271 | 9/1997 | |
| SU | 1718857 | 3/1992 | |
| WO | WO 82/04390 | 12/1982 | |
| WO | WO 90/14796 | 12/1990 | |
| WO | WO 92/10218 | 6/1992 | |
| WO | WO 92/19162 | 11/1992 | |
| WO | WO 93/17635 | 9/1993 | |
| WO | WO 94/17747 | 8/1994 | |
| WO | WO 96/09795 | 4/1996 | |
| WO | WO 96/14805 | 5/1996 | |
| WO | WO 97/35533 | 10/1997 | |
| WO | WO 98/14134 | 4/1998 | |
| WO | WO 00/07520 | 2/2000 | |

OTHER PUBLICATIONS

Parviz K. Amid et al., "Experimental evaluation of a new composite mesh with the selective property of incorporation to the abdominal wall without adhering to the intestines", Journal of Biomedical Materials Research, vol. 28, 373–375 (1994).

Robert G. Uzzo et al., "The Effects of Mesh Bioprosthesis on the Spermatic Cord Structures: A Preliminary Report in a Canine Model", The Journal Of Urology, Apr. 1999, vol. 161, pp. 1344–1349.

Gregory L. Brown, M.D. et al., "Comparison of Prosthetic Materials for Abdominal Wall Reconstruction in the Presence of Contamination and infections", Annals of Surgery, Jun. 1985, vol. 201, pp. 705–711.

Scott D. Jenkins, M.D. et al., A Comparison of Prosthetic Materials Used to Repair Abdominal Wall Defects:, Surgery, Aug. 1983, vol. 94, No. 2, pp. 392–398.

Hernando Cordona, M.D., "Prosthokeratoplasty", 1983, Cornea, vol. 2, No. 3, 1983, pp. 179–183.

Interceed(TC7) Adhesion Barrier Study Group (Cohen, Stephen M., et al.), Prevention of postsurgical adhesions by Interceed(TC7),*an absorbable adhesion barrier: a prospective, randomized multicenter clinical study, Fertility and Sterility, vol. 51, No. 6, Jun. 1989.

Alonzo P. Walker, M.D., James Henderson, D.V.M. and Robert E. Condon, M.D., "Double–Layer Prostheses for Repair of Abdominal Wall Defects in a Rabbit Model.", Jun. 1992.

* cited by examiner

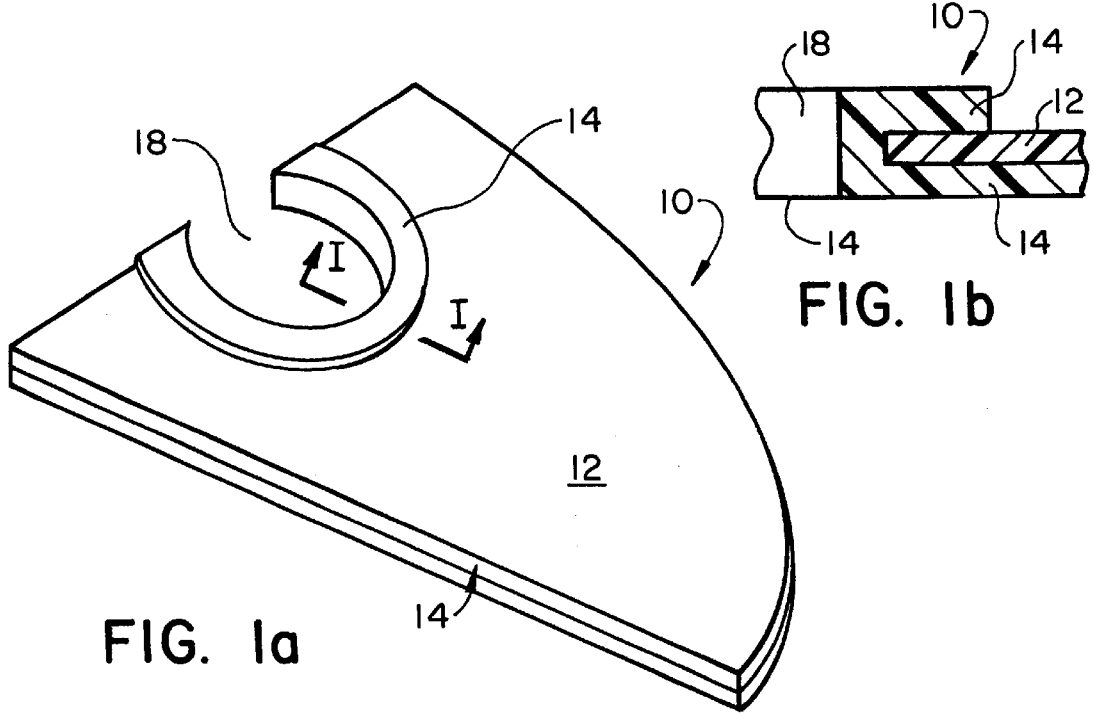
FIG. 1b
FIG. 1a
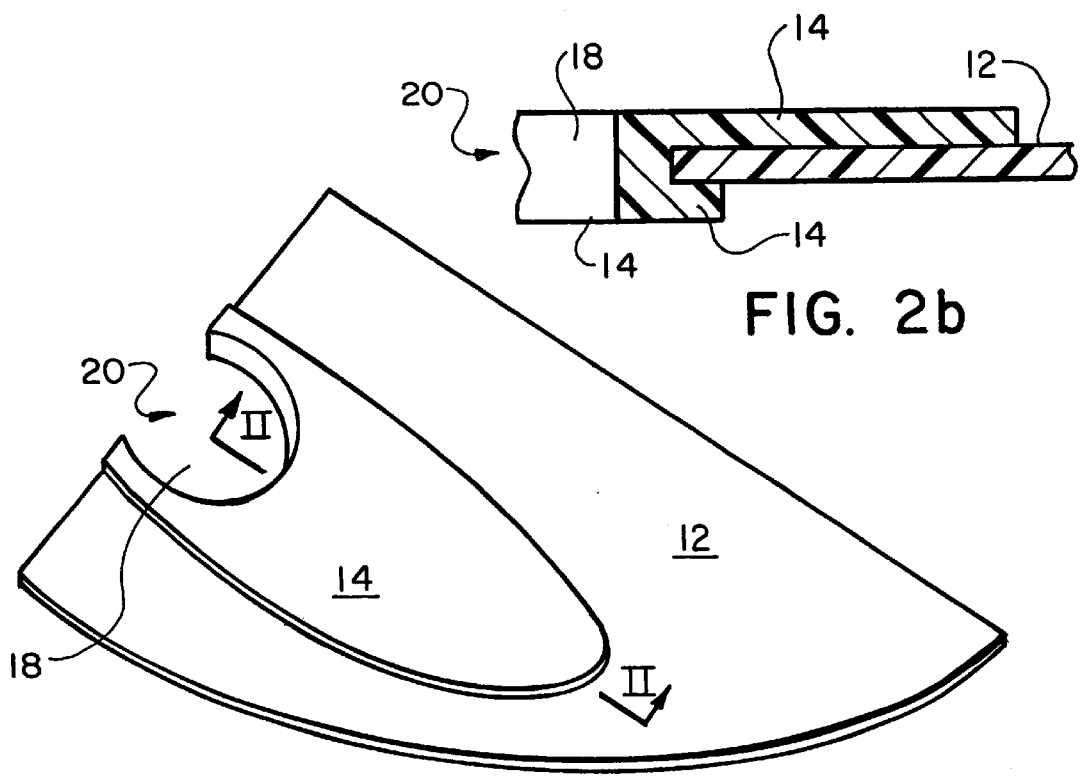
FIG. 2b
FIG. 2a

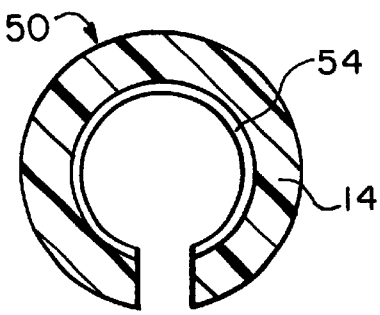
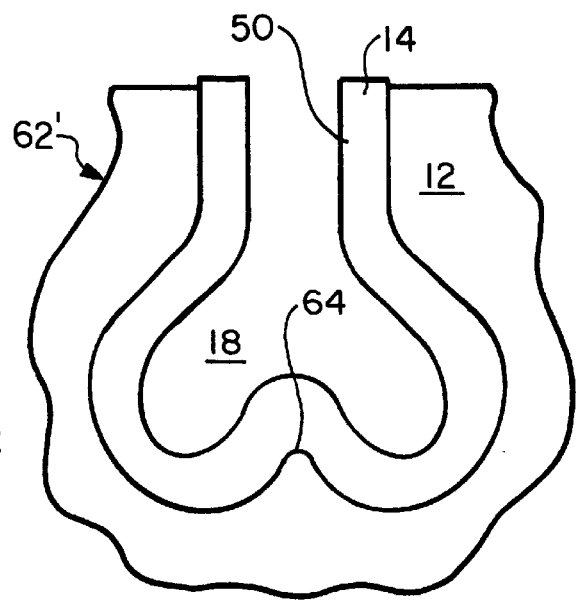
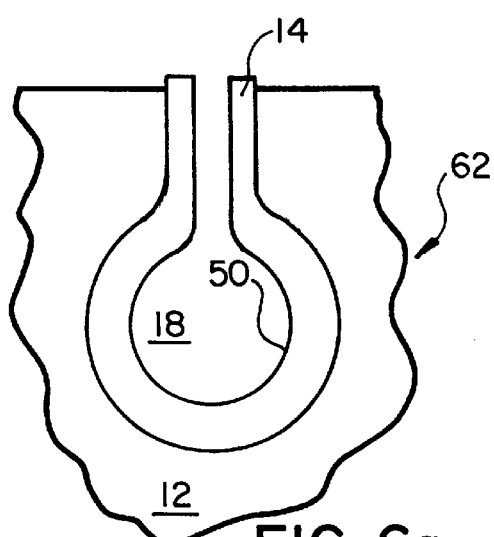
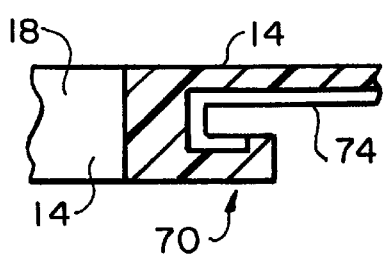
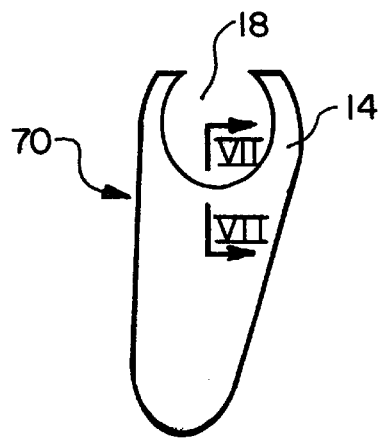
FIG. 5a
FIG. 5b
FIG. 6a
FIG. 6b
FIG. 7a
FIG. 7b

HERNIA PROSTHESIS

This application claims the benefit of U.S. Provisional Patent Application Ser. No. 60/146,061 filed on Jul. 28, 1999 entitled "Inguinal Hernia Patch".

BACKGROUND OF THE INVENTION

1. Field of the Invention

The present invention relates to a prosthesis for hernia repair. In particular, the present invention relates to a prosthesis for hernia repair configured to protect a cord passing through the prosthesis, such as the spermatic cord when the prosthesis is employed in an inguinal hernia repair.

2. Discussion of Related Art

Various prosthetic materials have been proposed to reinforce the abdominal wall and to close abdominal wall defects. In certain procedures, the prosthetic fabric may come into contact with sensitive tissue or organs potentially leading to postoperative adhesions between the mesh and the sensitive tissue or organs. There has been a suggestion that, in an inguinal hernia repair, the prosthetic fabric may come into direct contact with the spermatic cord. Postoperative adhesions between the mesh and the spermatic cord and/or erosion of the mesh into the cord, were they to occur, could potentially affect spermatic cord structure and function. For example, tissue ingrowth could potentially result in infertility, pain or other detrimental effects due to strangulation of the spermatic cord.

Uzzo et al., "The Effects of Mesh Bioprosthesis on the Spermatic Cord Structures: A Preliminary Report in a Canine Model", The Journal of Urology, Vol. 161, April 1999, pp. 1344–1349, suggests that the interposition of autologous fat between the mesh and the cord during open inguinal repair may prove beneficial. It had been proposed in U.S. Pat. No. 5,593,441, assigned to C.R. Bard, Inc., also the assignee of the present application, to repair ventral hernias and/or reconstruct chest walls using a prosthesis that is covered with an adhesion resistant barrier, such as a sheet of expanded PTFE. In the repair of ventral hernias and in chest wall reconstruction, the composite is positioned with the barrier relative to the region of potential adhesion, such as the abdominal viscera. Other configurations of composite prostheses can be found in U.S. Pat. Nos. 5,725,577 and 5,743,917, both of which are also assigned to C.R Bard, Inc.

International Publication No. WO 97/35533, by the present Applicant and also assigned to C.R. Bard, Inc., proposed a universal composite prosthesis in which one side of a layer of mesh material is completely covered with a layer of barrier material. The mesh material promotes biological tissue ingrowth while the barrier material retards biological tissue adherence thereto. The prosthesis may be utilized for various surgical procedures, including ventral hernia repair and inguinal hernia repair.

It is an object of the present invention to provide an improved method and prosthesis for the repair of hernias.

SUMMARY OF THE INVENTION

The present invention is a prosthesis and a method for mending a tissue or muscle wall defect, and has particular application in inguinal canal repairs near the spermatic cord. The prosthesis comprises a layer of repair fabric having a cord opening therethrough that is adapted to receive a cord-like structure, such as the spermatic cord, when the prosthesis is implanted at the repair site. The prosthesis also includes a cord protector that is attachable to the repair fabric at the cord opening to isolate the cord-like structure from at least the fabric in proximity to the cord opening. The repair fabric may be formed from a material which is susceptible to the formation of adhesions with sensitive tissue and organs. The cord protector may be formed from material which inhibits the formation of adhesions with sensitive tissue and organs.

In one embodiment of the invention, the repair fabric includes first and second surfaces and an opening having an edge that is defined by a portion of the layer of repair fabric. The cord protector covers a substantial portion of the edge to isolate the substantial portion of the edge from the cord-like structure.

In another embodiment of the invention, a layer of mesh fabric has a keyhole opening therethrough, and the cord protector extends about the keyhole opening and overlaps a portion of the layer of mesh fabric on opposing first and second surfaces thereof at least proximate the keyhole opening. The cord protector is adapted to receive the cord-like structure therethrough so that the layer of fabric is isolated from the cord-like structure by the cord protector at least proximate the keyhole opening.

The cord protecting material may extend away from the opening edge on the first surface and/or the second surface of the repair fabric. Additionally, the cord protector may extend substantially farther away from the opening edge on one of the first and second surfaces than on the other of the first and second surfaces. Further, the cord protector may substantially cover one of the first and second surfaces.

The prosthesis may be provided as a composite in which the cord protector is preattached to the repair fabric. Alternatively, the cord protector may be configured as an insert that is separate from and attachable to a prosthesis by a surgeon. This allows a surgeon to either retrofit a barrierless inguinal hernia prosthesis or to employ an implantable repair fabric that may have various tissue or muscle wall defect repair applications.

In a further embodiment of the invention, a cord protector is provided for use with a hernia prosthesis having a cord opening therethrough that is adapted to receive a cord-like structure. The cord protector includes a cord protecting insert that inhibits the formation of adhesions with sensitive tissue and organs. The cord protecting insert is constructed and arranged to be attached to at least a portion of the opening edge of the opening edge to isolate the cord-like structure from at least the opening edge of the hernia prosthesis.

The cord protecting insert may include a backbone member. The cord protecting insert may include a flexible tube having a slot along a length thereof that is adapted to receive a portion of the hernia prosthesis along the cord opening.

Other objects and features of the invention will become apparent from the following detailed description when taken in conjunction with the accompanying drawings. It is to be understood that the drawings are designed for the purpose of illustration only and are not intended as a definition of the limits of the invention.

BRIEF DESCRIPTION OF THE DRAWINGS

The foregoing and other objects and advantages of the invention will be appreciated more fully from the following drawings, wherein like reference characters designate like features, in which:

FIG. 1a is a perspective view of a prosthesis according to a first embodiment of the present invention;

FIG. 1b is a cross-sectional view of a portion of the prosthesis taken along section line I—I in FIG. 1a;

FIG. 2a is a perspective view of a prosthesis according to a second embodiment of the present invention;

FIG. 2b is a cross-sectional view of a portion of the prosthesis taken along section line II—II in FIG. 2a;

FIG. 3b is a cross-sectional view of a portion of the prosthesis taken along section line III—III in FIG. 3a;

FIG. 4b is a cross-sectional view of the cord protecting insert taken along section line IV—IV in FIG. 4a;

FIG. 5a is a perspective view of a cord protecting insert according to another embodiment of the present invention;

FIG. 5b is a cross-sectional view of the cord protecting insert taken along a helical line V—V in FIG. 5a;

FIG. 6a illustrates another embodiment of a prosthesis utilizing the cord protecting insert of FIGS. 5a and 5b;

FIG. 6b illustrates a further embodiment of a prosthesis utilizing the cord protecting insert of FIGS. 5a and 5b;

FIG. 7a is a plan view of a cord protecting insert according to another embodiment of the present invention; and FIG. 7b is a cross-sectional view of a portion of the cord protecting insert taken along section line VII—VII in FIG. 7a.

DESCRIPTION OF ILLUSTRATIVE EMBODIMENTS

Figure 3A:
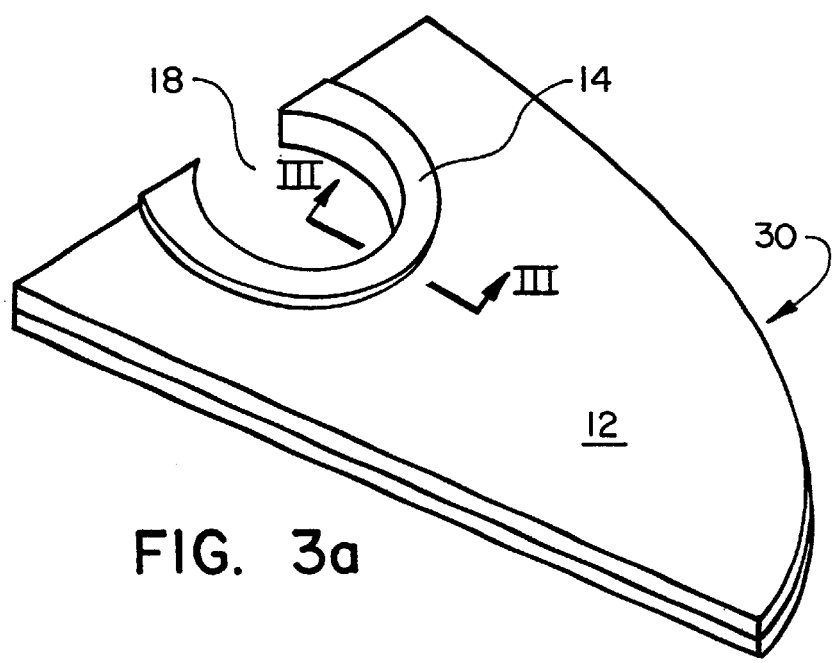
FIG. 3a is a perspective view of a prosthesis according to a third embodiment of the present invention.

FIGS. 1a–1b illustrate one embodiment of a prosthesis 10 which is particularly suited for inguinal hernia repair. The prosthesis 10 includes a layer of repair fabric 12 formed of a material which is susceptible to the formation of adhesions with sensitive tissue and organs. Opposed from the layer of repair fabric 12 is a barrier layer 14 generally formed of a material which inhibits the formation of adhesions with sensitive tissue and organs.

The prosthesis 10 is configured with a cord opening or keyhole 18 therethrough for receipt of the spermatic cord for inguinal hernia repair. The barrier layer 14 extends through and surrounds the cord opening 18 and covers the opening edge to isolate the spermatic cord from the opening edge of the fabric. The barrier layer 14 may be configured to overlap one or both surfaces of the layer of repair fabric 12 in the area around the cord opening 18. As illustrated, the barrier layer 14 covers one surface of the layer of repair fabric 12 and overlaps a portion of the other surface of the fabric in close proximity to the cord opening 18. The overlapping of the layer 12 around the cord opening 18 by the barrier layer 14 may enhance the isolation of the spermatic cord from the layer of repair fabric as it passes through the prosthesis. This construction provides a composite prosthesis in which the surgeon does not have to fold the prosthesis at the edges during an inguinal hernia operation in order to place the barrier layer 14 in the desired position.

The layer of repair fabric 12 and/or the barrier layer 14 may be configured to suit a particular repair procedure and/or provide particular adhesion/adhesion resistance characteristics. For example, the barrier layer may be configured to cover selected portions of the fabric so as to enhance tissue adhesion to particular portions of the prosthesis while limiting the incidence of tissue adhesion at other portions of the prosthesis to the spermatic cord and/or other sensitive tissue and organs in the repair region.

FIGS. 2a–2b illustrate another embodiment of a prosthesis 20 for inguinal hernia repairs. The prosthesis 20 includes a layer of repair fabric 12, a barrier layer 14 and a cord opening 18 for the spermatic cord. In contrast to the prosthesis 10 illustrated in FIGS. 1a–1b, the barrier layer 14 is configured to overlie selected portions of the fabric 12. As best shown in FIG. 2b, the barrier layer 14 surrounds the opening 18 and extends farther away from the opening 18 along a portion of one surface of the fabric 12 along which the spermatic cord may contact the prosthesis. The barrier layer 14 acts as a cord protector that may be provided in those areas of the prosthesis 20 expected to contact the spermatic cord.

Figure 3B:
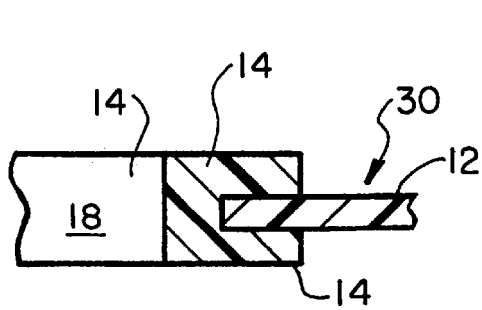

FIGS. 3a–3b illustrate a further embodiment of a prosthesis 30 for inguinal hernia repairs. The prosthesis 30 includes a layer of mesh fabric 12, a barrier layer 14 and a cord opening for receipt of the spermatic cord. As illustrated, the barrier layer 14, or the cord protector, is limited to overlying portions of the fabric in close proximity to the opening 18. This configuration would be expected to increase tissue adhesion to the prosthesis while limiting cord adhesion in the vicinity of the opening.

In one embodiment, the layer of repair fabric 12 is formed of a polyolefin material, such as a sheet of knitted polypropylene monofilament mesh fabric. One example of a suitable material is BARD MESH available from C.R. Bard, Inc. When implanted, the polypropylene mesh promotes rapid tissue ingrowth into and around the mesh structure. Other surgical materials which are suitable for tissue reinforcement and defect closure may be utilized including PROLENE, SOFT TISSUE PATCH (microporous ePTFE), URGIPRO, TRELEX, ATRIUM and MERSELENE. Polyethylene may also form an acceptable polyolefin material for the layer 12. Absorbable materials, including polyglactin (VICRYL) and polyglycolic acid (DEXON), also may be suitable. It also is contemplated that the mesh fabric may be formed from multifilament yarns and that woven, molded and other suitable methods of forming prosthetic mesh materials may be employed. It is to be appreciated that any suitable materials promoting fibroplasia may be used as would be apparent to one of skill in the art.

In one embodiment, the barrier layer 14 is formed from a fluoropolymer material such as polytetrafluoroethylene (PTFE). One example of a suitable material is a sheet of expanded polytetrafluoroethylene (ePTFE), such as GORE-TEX available from W.L. Gore & Associates, Inc., having a pore size (submicronal) that discourages tissue ingrowth and adhesion. Fluorinated ethylene propylene (FEP), tetrafluoroethylene (TFE) and ethylene tetrafluoroethylene (ETFE) are other acceptable fluoropolymers.

A representative and non-limiting sampling of other suitable barrier materials includes silicone elastomer, such as SILASTIC Rx Medical Grade Sheeting (Platinum Cured) distributed by Dow Corning Corporation, TEFLON mesh, and microporous polypropylene sheeting (CELGARD). It is also contemplated that a polyethylene terephthalate, such as DACRON and MYLAR, may be employed as a barrier material. Autogenous, heterogenous and xenogeneic tissue also are contemplated including, for example, pericardium and small intestine submucosa. Absorbable materials, such as oxidized, regenerated cellulose (Intercede (TC7)) may be employed for some applications. It is to be appreciated that any suitable adhesion resistant materials may be used as would be apparent to one of skill in the art.

Figure 4B:
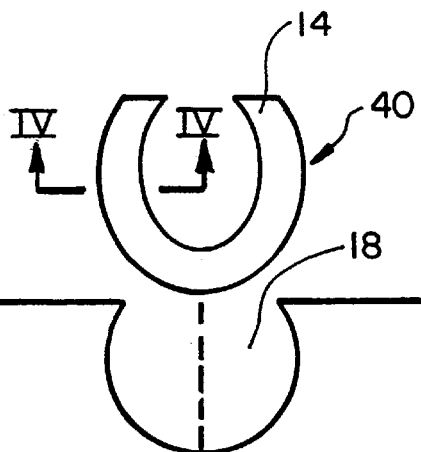
Figure 4B:
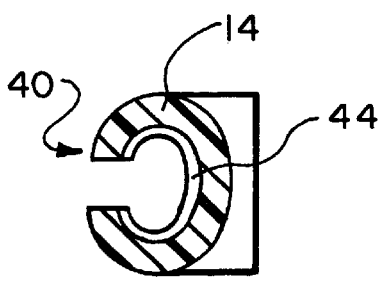
Figure 4A:
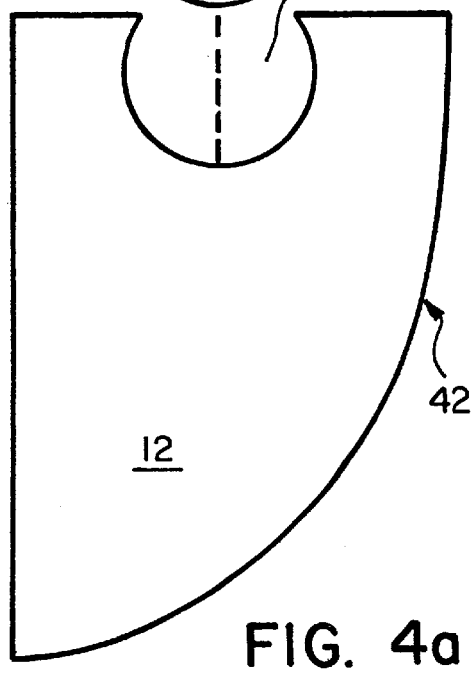
FIG. 4a is an exploded plan view of a barrier-less prosthesis and a separate cord protecting insert according to a fourth embodiment of the present invention.

In some instances, a surgeon may find it desirable to employ a cord protector that can be readily attached to a hernia repair prosthesis that is initially provided with no adhesion resistant barrier. FIGS. 4a–4b illustrate one embodiment of a prosthesis utilizing a separable cord protecting insert 40 which is attachable to a barrier-less inguinal hernia patch 42 formed with a layer of repair fabric 12 that is susceptible to the formation of adhesions with sensitive tissue and organs. The patch 42 includes a cord opening 18 for receipt of the spermatic cord. The cord protecting insert 40 is adapted to overlap and surround the opening 18 in a manner similar to the prosthesis 30 discussed above.

In one embodiment, the separable or attachable cord protecting insert 40 includes an outer barrier layer 14 and a support member or backbone 44 which can be used to maintain the shape of the cord protecting insert 40. The backbone 44 can also be utilized to provide the cord protecting insert 40 with sufficient rigidity that allows it to frictionally engage the patch 42. It is to be appreciated that any suitable arrangement as would be apparent to one of skill may be employed to attach the cord protecting insert to the fabric. For example, biological adhesives may also be utilized to bond the cord protecting insert 40 to the barrier-less prosthesis 42. The cord protecting insert 40 allows existing hernia patches 42 to be easily modified to provide spermatic cord protection.

The cord protecting insert may be constructed in a manner that allows it to be readily attachable to repair fabric. In one embodiment illustrated in FIGS. 5a and 5b, the cord protecting insert 50 includes a long flexible tube having a slot along the length of the tube for receipt of a portion of the fabric along a keyhole or opening of a hernia patch. The cord protecting insert 50 may include a backbone 54 in the form of a spiral thread or wire extending along the inside of the cord protecting insert 50. Of course, the spiral threads forming the backbone 54 are discontinuous due to the slot in the tube. It is to be appreciated that the cord protecting insert may employ any suitable configuration.

The flexible cord protecting insert 50 may be particularly suited to retrofitting hernia repair patches having a cord opening of various configurations. FIG. 6a illustrates the cord protecting insert 50 attached along the opening edge of a hernia patch 62 provided with a cord opening 18 having a keyhole shape. FIG. 6b illustrates the cord protecting insert 50 attached along the opening edge of a hernia patch 62' with a cord opening 18 having an additional flap 64 provided for receipt of the spermatic cord. The cord protecting attributes of the cord protecting insert 50 make the receipt of the spermatic cord onto the flap 64 a viable possibility.

As would be readily apparent to one of skill, the cord protecting insert may employ any configuration suitable for providing desired cord protection characteristics. FIGS. 7a–7b illustrate another embodiment of a cord protecting insert 70 that may be attached to a barrierless hernia patch. The cord protecting insert 70 is similar in shape to the barrier layer 14 of hernia patch 20 illustrated in FIGS. 2a–2b discussed above. The cord protecting insert 70 is adapted to fit around a cord opening 18 of a hernia patch and includes a barrier layer 14 and a backbone 74 which is adapted to give the appropriate rigidity to the cord protecting insert 70 and provide for easy attachment to a barrier-less hernia patch. The cord protecting insert 70 includes an extension that is configured to overlie one side of the patch in a position likely to engage the spermatic cord.

It is to be appreciated that the separable cord protecting inserts of FIGS. 4–7 provide protective characteristics similar to those of the barrier layers 14 employed with the composite prostheses illustrated in FIGS. 1–3. In this regard, the barrier layers 14 of FIGS. 1–3 may be considered as cord protecting inserts that are integral with the prosthesis formed by the layer of repair fabric 12. The separate cord protecting inserts of FIGS. 4–7 allow for retrofitting existing barrier-less hernia prosthetics.

It will be apparent that other embodiments and various modifications may be made to the present invention without departing from the scope thereof. For example, the cord protecting inserts may be formed of a material not requiring a separate backbone or supporting member. Further, inguinal hernia patches having alternative shapes may also be contemplated within the scope of the present invention. The foregoing description of the invention is intended merely to be illustrative and not restrictive thereof. The scope of the present invention is defined by the appended claims and equivalents thereto.

What is claimed is:

1. A hernia prosthesis for repairing a tissue or muscle wall defect, the prosthesis comprising:
   a layer of repair fabric including first and second surfaces and an opening therethrough that is adapted to receive a cord-like structure, the opening having an edge that is defined by a portion of the layer of repair fabric; and
   a cord protector that is attached to the layer of repair fabric across a substantial portion of the edge to cover and isolate the substantial portion of the edge from the cord-like structure.

2. The hernia prosthesis according to claim 1, wherein the layer of repair fabric is susceptible to the formation of adhesions with sensitive tissue and organs.

3. The hernia prosthesis according to claim 2, wherein the layer of repair fabric is formed from a polyolefin.

4. The hernia prosthesis according to claim 1, wherein the layer of repair fabric includes a plurality of interstices that allow tissue ingrowth.

5. The hernia prosthesis according to claim 4, wherein the fabric is formed from polypropylene.

6. The hernia prosthesis according to claim 2, wherein the cord protector inhibits the formation of adhesions with sensitive tissue and organs.

7. The hernia prosthesis according to claim 2, wherein the cord protector is formed from a fluoropolymer.

8. The hernia prosthesis according to claim 7, wherein the cord protector is formed from expanded PTFE.

9. The hernia prosthesis according to claim 1, wherein the cord protector overlies portion of at least one of the first and second surfaces of the layer of repair fabric.

10. The hernia prosthesis according to claim 9, wherein the cord protector overlies a portion of the first and second surfaces of the layer of repair fabric.

11. The hernia prosthesis according to claim 10, wherein the cord protector extends substantially farther away from the edge on one of the first and second surfaces than the other of the first and second surfaces.

12. The hernia prosthesis according to claim 9, wherein the cord protector substantially covers the at least one of the first and second surfaces.

13. The hernia prosthesis according to claim 1, wherein the cord protector is a portion of a cord protecting insert that is attachable to the layer of repair fabric.

14. The hernia prosthesis according to claim 1, wherein the cord protector is integrally formed with the layer of repair fabric.

15. The hernia prosthesis according to claim 1, wherein the layer of repair fabric is constructed and arranged to mend an inguinal hernia, the cord protector being configured to isolate the substantial portion of the edge from the spermatic cord.

16. A hernia prosthesis for repairing a tissue or muscle wall defect, the prosthesis comprising:

a layer of repair fabric including first and second surfaces and an opening therethrough that is adapted to receive a cord-like structure, the opening having an edge that is defined by a portion of the layer of repair fabric; and a cord protector covering a substantial portion of the edge to isolate the substantial portion of the edge from the cord-like structure, wherein the cord protector includes a backbone member.

17. A hernia prosthesis for repairing a tissue or muscle wall defect, the prosthesis comprising:

a layer of repair fabric including first and second surfaces and an opening therethrough that is adapted to receive a cord-like structure, the opening having an edge that is defined by a portion of the layer of repair fabric; and a cord protector covering a substantial portion of the edge to isolate the substantial portion of the edge from the cord-like structure, wherein the cord protector includes a flexible tube having a slot extending along a length thereof, the slot being adapted to receive a portion of the layer of repair fabric along the opening.

18. A cord protector for use with a hernia prosthesis having a cord opening therethrough that is adapted to receive a cord-like structure, the cord opening being defined by an opening edge along a portion of the hernia prosthesis, the cord protector comprising:

a cord protecting insert that inhibits the formation of adhesions with sensitive tissue and organs, the cord protecting insert constructed and arranged to be attached to the hernia prosthesis along at least a portion of the opening to isolate the cord-like structure from at least the opening edge of the hernia prosthesis. the hernia prosthesis.

19. The spermatic cord protector according to claim 18, wherein the insert is attachable to the hernia prosthesis around the cord opening.

20. The spermatic cord protector according to claim 18, wherein the cord protecting insert is formed from expanded PTFE.

21. The spermatic cord protector according to claim 18, wherein the cord protecting insert is constructed and arranged to overlap at least a portion of the hernia prosthesis around the cord opening.

22. The spermatic cord protector according to claim 21, wherein the cord protecting insert is constructed and arranged to overlie a portion of a first surface and a portion of a second surface of the hernia prosthesis.

23. The spermatic cord protector according to claim 22, wherein the cord protecting insert includes an extension that is constructed and arranged to extend substantially farther away from the cord opening on one of the first and second surfaces than the other of the first and second surfaces.

24. The spermatic cord protector according to claim 22, wherein the cord protecting insert is constructed and arranged to substantially cover one of the first and second surfaces.

25. The spermatic cord protector according to claim 18, wherein the cord protecting insert is attachable to the hernia prosthesis with an adhesive.

26. The spermatic cord protector according to claim 18, wherein the cord protecting insert includes a backbone member attached thereto.

27. The spermatic cord protector according to claim 18, wherein the cord protecting insert includes a flexible tube having a slot along a length thereof, the slot being adapted to receive a portion of the hernia prosthesis along the cord opening.

28. The spermatic cord protector according to claim 27, wherein the tube includes a backbone member.

29. The spermatic cord protector according to claim 18, wherein the cord protecting insert is configured to grip the hernia prosthesis and frictionally engage the hernia prosthesis around the opening of the hernia prosthesis.

30. An inguinal hernia repair prosthesis comprising:

a layer of mesh fabric having a cord opening therethrough that is adapted to receive the spermatic cord therethrough, the cord opening being defined by an opening edge along a portion of the layer of mesh fabric; and a cord protector that inhibits the formation of adhesions with sensitive tissue and organs, the cord protector extending about the cord opening and overlapping a portion of the layer of mesh fabric on opposing first and second surfaces thereof and extending therebetween over the opening edge of the cord opening, the opening edge of the layer of mesh fabric to be isolated from the spermatic cord by the cord protector.

31. The inguinal hernia prosthesis according to claim 30, wherein the layer of mesh fabric is formed from polypropylene.

32. The inguinal hernia prosthesis according to claim 30, wherein the cord protector is formed from expanded PTFE.

33. The inguinal hernia prosthesis according to claim 30, wherein the cord protector extends away from the cord opening on the first surface and the second surface of the layer of mesh fabric.

34. The inguinal hernia prosthesis according to claim 33, wherein the cord protector extends substantially farther away from the cord opening on one of the first and second surfaces than on the other of the first and second surfaces.

35. The inguinal hernia prosthesis according to claim 30, wherein the cord protector is integrated with the layer of mesh fabric to form a composite prosthesis.

36. The inguinal hernia prosthesis according to claim 30, further comprising a backbone member attached to the cord protector.

37. The inguinal hernia prosthesis according to claim 30, wherein the cord protector includes a flexible tube having a slot along a length thereof, a portion of the layer of mesh fabric surrounding the cord opening being received in the slot to attach the cord protector to the layer of mesh fabric.

38. The inguinal hernia prosthesis according to claim 30, wherein the cord opening is a keyhole opening.

39. A method of repairing a hernia defect near a cord-like structure, the method comprising steps of:

providing a prosthesis including a layer of repair fabric with first and second surfaces and an opening therethrough that is adapted to receive the cord-like structure, the opening having an edge that is defined by a portion of the layer of repair fabric, the prosthesis further including a cord protector that is attached to the layer of repair fabric across a substantial portion of the edge to cover and isolate the substantial portion of the edge from the cord-like structure; and implanting the prosthesis to cover the hernia defect with the cord-like structure passing through the opening and being isolated from the edge by the cord protector which is positioned between the cord-like structure and the edge.

40. The method according to claim 39, wherein the layer of repair fabric is susceptible to the formation of adhesions with sensitive tissue and organs.

41. The method according to claim 40, wherein the cord protector inhibits the formation of adhesions with sensitive tissue and organs.

42. A method of repairing a hernia defect near a cord-like structure, the method comprising steps of:

provided a prosthesis including a layer of repair fabric with first and second surfaces and an opening therethrough that is adapted to receive the cord-like structure, the opening having an edge that is defined by a portion of the layer of repair fabric, the prosthesis further including a cord protector covering a substantial portion of the edge to isolate the substantial portion of the edge from the cord-like structure;

attaching the cord protector to the layer of repair fabric; and implanting the prosthesis to cover the hernia defect with the cord-like structure passing through the opening and being isolated from the edge by the cord protector which is positioned between the cord-like structure and the edge.

43. The method according to claim 39, wherein the prosthesis is implanted in the inguinal canal to mend an inguinal hernia, the spermatic cord being passed through the opening and being isolated from the edge by the cord protector.

* * * * *